(12) United States Patent
Lai et al.

(10) Patent No.: US 10,308,922 B2
(45) Date of Patent: Jun. 4, 2019

(54) METHODS OF PROCESSING TEXTILES USING POLYPEPTIDES HAVING ENDOGLUCANASE ACTIVITY

(71) Applicant: Novozymes A/S, Bagsvaerd (DK)

(72) Inventors: Weijian Lai, Beijing (CN); Lan Tang, Beijing (CN); Marc Dominique Morant, Bagsvaerd (DK); Paul Harris, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/896,704

(22) Filed: Feb. 14, 2018

(65) Prior Publication Data

US 2018/0179506 A1    Jun. 28, 2018

Related U.S. Application Data

(62) Division of application No. 14/917,390, filed as application No. PCT/CN2014/089332 on Oct. 23, 2014, now Pat. No. 9,926,548.

(30) Foreign Application Priority Data

Oct. 25, 2013    (WO) ............... PCT/CN2013/085993

(51) Int. Cl.
*D06M 16/00*    (2006.01)
*D06M 101/04*    (2006.01)
*D06M 101/06*    (2006.01)
*C12N 9/42*    (2006.01)

(52) U.S. Cl.
CPC ......... *C12N 9/2437* (2013.01); *D06M 16/003* (2013.01); *C12Y 302/01004* (2013.01); *D06M 2101/04* (2013.01); *D06M 2101/06* (2013.01); *D06M 2200/35* (2013.01)

(58) Field of Classification Search
CPC .............. C12N 9/2437; D06M 16/003; D06M 2200/35; D06M 2101/06; D06M 2101/04; C12Y 302/01004
See application file for complete search history.

(56) References Cited

U.S. PATENT DOCUMENTS

| 6,001,639 A | 12/1999 | Schulein et al. |
| 9,238,806 B2 * | 1/2016 | Hill .................. C12N 9/2437 |
| 2014/0080178 A1 | 3/2014 | Schnorr et al. |

FOREIGN PATENT DOCUMENTS

| CN | 101974491 | 2/2011 |
| CN | 102732540 | 10/2012 |
| CN | 103060289 | 4/2013 |
| WO | 1996029397 A1 | 9/1996 |
| WO | 2009/010444 A2 | 1/2009 |
| WO | 2010/076388 A1 | 7/2010 |
| WO | 2012/106824 A1 | 8/2012 |

OTHER PUBLICATIONS

Schulte et al., EMBL Access No. CAD70529 (2006).
Ellison et al., UniProt Accession No. F8MVQ2 (2011).
Shimonaka et al, Bioscience, Biotechnology and Biochemistry, vol. 70, No. 10, pp. 2460-2466 (2006).
Branden et al, 1991, Introduction to protein structure, 247.
Ellison et al, 2011, GenBank accession No. EGO54803.
Ellison et al, 2011, GenBank accession No. GL891307.
Galagan et al, 2008, Genbank access No. XM_952014.
Galagan et al, 2008, Genbank access No. XP-957107.
Sadowski et al, 2009, Curr Op Struct Biol 19, 357-362.
Seffernick et al, 2001, J Bacteriol 183(8), 2405-2410.
Witkowski et al, 1999, Biochemistry 38, 11643-11650.
Shimonaka et al, 2006, Biosci Biotech Biochem, vol. 70 No. 10, pp. 2460-2466.

* cited by examiner

*Primary Examiner* — Delia M Ramirez
(74) *Attorney, Agent, or Firm* — Eric J. Fechter

(57) ABSTRACT

The present invention relates to polypeptides having endoglucanase activity, catalytic domains, and polynucleotides encoding the polypeptides or catalytic domains. The invention also relates to nucleic acid constructs, vectors, and host cells comprising the polynucleotides as well as methods of producing and using the polypeptides or catalytic domains.

18 Claims, No Drawings

Specification includes a Sequence Listing.

METHODS OF PROCESSING TEXTILES USING POLYPEPTIDES HAVING ENDOGLUCANASE ACTIVITY

CROSS-REFERENCE TO RELATED APPLICATIONS

This application is a divisional of U.S. patent application Ser. No. 14/917,390, now U.S. Pat. No. 9,926,548, which is a 35 U.S.C. 371 national application of international application no, PCT/CN2014/089332 filed Oct. 23, 2014, which claims priority or the benefit under 35 U.S.C. 119 of international application no. PCT/CN2013/085993 filed Oct. 25, 2013. The contents of these applications are fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

Field of the Invention

The present invention relates to polypeptides having endoglucanase activity, catalytic domains, and cellulose binding domains, and polynucleotides encoding the polypeptides, catalytic domains, and cellulose binding domains. The invention also relates to nucleic acid constructs, vectors, and host cells comprising the polynucleotides as well as methods of producing and using the polypeptides, catalytic domains, and cellulose binding domains.

Description of the Related Art

Cellulases or cellulytic enzymes are enzymes involved in hydrolyses of cellulose. It is known that there are three major types of cellulase enzymes involved, namely endoglucanase, cellobiohydrolase, and beta-glucosidase.

There is a wide spectrum of industrial applications of cellulases. In the textile industry, cellulases are used in denim finishing to create a fashionable stone washed appearance on denim cloths using a biostoning process. Cellulases are also used, for instance, to clean fuzz and prevent formation of pills on the surface of cotton garments using a biopolishing process.

WO9629397 discloses enzyme preparations with performance in industrial applications such as laundry composition, for biopolishing of newly manufactured textiles, for providing an abraded look of cellulosic fabric or garment, and for treatment of paper pulp.

WO2010/076388 discloses fungal endoglucanases with substantial performance at low temperatures; the endoglucanases are used for treating cellulosic material, especially in textile industry, e.g. in biofinishing or biostoning.

There are continued needs in the art for new endoglucanases and methods for obtaining a cellulosic textile fabric with good abrasion effect, and/or reduced tendency to pilling formation in the biopolishing process, especially at low temperature.

The present invention aims to meet these needs.

SUMMARY OF THE INVENTION

The present invention relates to polypeptides having endoglucanase activity selected from the group consisting of:

(a) a polypeptide having at least 99% sequence identity to the mature polypeptide of SEQ ID NO: 2;

(b) a polypeptide encoded by a polynucleotide that hybridizes very high stringency conditions with (i) the mature polypeptide coding sequence of SEQ ID NO: 1, (ii) the cDNA sequence thereof, or (iii) the full-length complement of (i) or (ii);

(c) a polypeptide encoded by a polynucleotide having at least 99% sequence identity to the mature polypeptide coding sequence of SEQ ID NO: 1 or the cDNA sequence thereof;

(d) a variant of the mature polypeptide of SEQ ID NO: 2 comprising a substitution, deletion, and/or insertion at one or more (e.g., several) positions; and (e) a fragment of the polypeptide of (a), (b), (c), or (d) that has endoglucanase activity.

The present invention also relates to polypeptides comprising a catalytic domain selected from the group consisting of:

(a) a catalytic domain having at least 99% sequence identity to amino acids 22 to 237 of SEQ ID NO: 2;

(b) a catalytic domain encoded by a polynucleotide that hybridizes under very high stringency conditions with (i) nucleotides 64 to 764 of SEQ ID NO: 1, (ii) the cDNA sequence thereof, or (iii) the full-length complement of (i) or (ii);

(c) a catalytic domain encoded by a polynucleotide having at least 99% sequence identity to nucleotides 64 to 764 of SEQ ID NO: 1 or the cDNA sequence thereof;

(d) a variant of amino acids 22 to 237 of SEQ ID NO: 2 comprising a substitution, deletion, and/or insertion at one or more (e.g., several) positions; and (e) a fragment of the catalytic domain of (a), (b), (c), or (d) that has endoglucanase activity.

The present invention also relates to a method for treating textile with a polypeptide having endoglucanase activity selected from the group consisting of:

(a) a polypeptide having at least 90% sequence identity to the mature polypeptide of SEQ ID NO: 2;

(b) a polypeptide encoded by a polynucleotide that hybridizes under high or very high stringency conditions with (i) the mature polypeptide coding sequence of SEQ ID NO: 1, or (ii) the full-length complementary strand of (i);

(c) a polypeptide encoded by a polynucleotide having at least 90% sequence identity to the mature polypeptide coding sequence of SEQ ID NO: 1;

(d) a variant of the mature polypeptide of SEQ ID NO: 2 comprising a substitution, deletion, and/or insertion at one or more (e.g., several) positions; and (e) a fragment of the polypeptide of (a), (b), (c), or (d) that has endoglucanase activity.

The present invention also relates to a polynucleotide encoding a signal peptide comprising or consisting of amino acids 1 to 21 of SEQ ID NO: 2, a polynucleotide encoding a propeptide comprising or consisting of amino acids 1 to 63 of SEQ ID NO: 2, each of which is operably linked to a gene encoding a protein; nucleic acid constructs, expression vectors, and recombinant host cells comprising the polynucleotides; and methods of producing a protein.

DEFINITIONS

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity may be determined using carboxymethyl cellulose (CMC) as substrate according to the procedure of part VI in page 264 of Ghose, 1987, *Pure and Appl. Chem.* 59: 257-268.

For purposes of the present invention, endoglucanase activity is determined according to the procedure described in the Examples. In one aspect, the polypeptides of the present invention have at least 60%, at least 70%, at least 80%, at least 90%, at least 95%, or at least 100% of the endoglucanase activity of the mature polypeptide of SEQ ID NO: 2 or SEQ ID NO: 4.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Binding domain: The term "cellulose binding domain" means the region of an enzyme that mediates binding of the enzyme to amorphous regions of a cellulose substrate. The cellulose binding domain (CBD) is typically found either at the N-terminal or at the C-terminal extremity of an endoglucanase. In the context, cellulose binding domain and carbohydrate binding modules are used interchangeable.

Catalytic domain: The term "catalytic domain" means the region of an enzyme containing the catalytic machinery of the enzyme.

Family 45 or Family GH45 or CEL45: The term "Family 45" or "Family GH45" or "CEL45" is defined herein as a polypeptide falling into the glycoside hydrolase Family 45 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. Carbohydrate binding modules are often associated with catalytic modules encoding enzymes such as glycosyl hydrolases. Guillén D, Sánchez S, Rodríguez-Sanoja R. Carbohydrate-binding domains: multiplicity of biological roles. Applied Microbiology & Biotechnology February 2010; 85(5):1241. Available from: EDS Foundation Index, Ipswich, Mass.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or cellulose binding domain having one or more (e.g., several) amino acids absent from the amino and/or carboxyl terminus of a mature polypeptide or domain; wherein the fragment has endoglucanase activity. In one aspect, a fragment contains 85%, 90%, and 95% of the number of amino acids of the mature polypeptide of SEQ ID NO: 2 or SEQ ID NO: 4.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 293 of SEQ ID NO: 2 and amino acids 22 to 293 of SEQ ID NO: 4 based on SignalP (Nielsen et al., 1997, *Protein Engineering* 10: 1-6) that predicts amino acids 1 to 21 of SEQ ID NO: 2 and amino acids 1 to 21 of SEQ ID NO: 4 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having endoglucanase activity. In one aspect, the mature polypeptide coding sequence is nucleotides 64 to 764 of SEQ ID NO: 1 and nucleotides 1 to 63 of SEQ ID NO: 1 encode a signal peptide. In one aspect, the mature polypeptide coding sequence is nucleotides 64 to 764 of SEQ ID NO: 3 and nucleotides 1 to 63 of SEQ ID NO: 3 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having endoglucanase activity.

Variant: The term "variant" means a polypeptide having endoglucanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Textile: The term "textiles" used herein is meant to include fibers, yarns, fabrics and garments.

Fabric can be constructed from fibers by weaving, knitting or non-woven operations. Weaving and knitting require yarn as the input whereas the non-woven fabric is the result of random bonding of fibers (felt can be thought of as non-woven). In the present context, the term "fabric" is also intended to include fibers and other types of processed fabrics.

According to the invention, the method of the invention may be applied to any textile known in the art (woven, knitted, or non-woven). In particular the process of the present invention may be applied to cellulose-containing or cellulosic textile, such as cotton, viscose, rayon, ramie, linen, lyocell (e.g., Tencel, produced by Courtaulds Fibers), or mixtures thereof, or mixtures of any of these fibers together with synthetic fibres (e.g., polyester, polyamid, nylon) or other natural fibers such as wool and silk, such as viscose/cotton blends, lyocell/cotton blends, viscose/wool blends, lyocell/wool blends, cotton/wool blends; flax (linen), ramie and other fabrics based on cellulose fibers, including all blends of cellulosic fibers with other fibers such as wool, polyamide, acrylic and polyester fibers, e.g., viscose/cotton/polyester blends, wool/cotton/polyester blends, flax/cotton blends etc.

DETAILED DESCRIPTION OF THE INVENTION

Polypeptides Having Endoglucanase Activity

In an embodiment, the present invention relates to polypeptides having a sequence identity to the mature polypeptide of SEQ ID NO: 2 of at least 99%, or 100%, which have endoglucanase activity. In one aspect, the polypeptides differ by up to 4 amino acids, e.g., 1, 2, 3, 4 or 5 from the mature polypeptide of SEQ ID NO: 2.

In an embodiment, the present invention relates to a method for treating textile with a polypeptide having a sequence identity to the mature polypeptide of SEQ ID NO: 2 or SEQ ID NO: 4 of at least 90%, 91%, 92%, 93%, 94%, 95%, 96%, 97%, 98%, 99% or 100%, which have endoglucanase activity. In one aspect, the polypeptides differ by up to 10 amino acids, e.g., 1, 2, 3, 4, 5, 6, 7, 8, 9, or 10 from the mature polypeptide of SEQ ID NO: 2 or SEQ ID NO: 4.

In an embodiment, the polypeptide has been isolated. A polypeptide of the present invention or a method for treating textile with polypeptide preferably comprises or consists of the amino acid sequence of SEQ ID NO: 2 or SEQ ID NO: 4 or an allelic variant thereof; or is a fragment thereof having endoglucanase activity. In another aspect, the polypeptide comprises or consists of the mature polypeptide of SEQ ID NO: 2 or SEQ ID NO: 4. In another aspect, the polypeptide comprises or consists of amino acids 22 to 293 of SEQ ID NO: 2 or amino acid 22 to 293 of SEQ ID NO: 4.

In another embodiment, the present invention relates to a polypeptide or a method for treating textile with polypeptide having endoglucanase activity encoded by a polynucleotide that hybridizes under high stringency conditions or very high stringency conditions with (i) the mature polypeptide coding sequence of SEQ ID NO: 1 or SEQ ID NO: 3, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.). In an embodiment, the polypeptide has been isolated.

The polynucleotide of SEQ ID NO: 1 or SEQ ID NO: 3 or a subsequence thereof, as well as the polypeptide of SEQ ID NO: 2 or SEQ ID NO: 4 or a fragment thereof, may be used to design nucleic acid probes to identify and clone DNA encoding polypeptides having endoglucanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having endoglucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or SEQ ID NO: 3; (ii) the mature polypeptide coding sequence of SEQ ID NO: 1 or SEQ ID NO: 3; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2 or SEQ ID NO: 4; the mature polypeptide thereof; or a fragment thereof. In another aspect, the nucleic acid probe is SEQ ID NO: 1 or SEQ ID NO: 3 or the cDNA sequence thereof.

In another embodiment, the present invention relates to a polypeptide having endoglucanase activity encoded by a polynucleotide having a sequence identity to the mature polypeptide coding sequence of SEQ ID NO: 1 or SEQ ID NO: 3 or the cDNA sequence thereof of at least 99%, or 100%. In a further embodiment, the polypeptide has been isolated.

In another embodiment, the present invention relates to variants of the mature polypeptide of SEQ ID NO: 2 or SEQ ID NO: 4 comprising a substitution, deletion, and/or insertion at one or more (e.g., several) positions. In an embodiment, the number of amino acid substitutions, deletions and/or insertions introduced into the mature polypeptide of SEQ ID NO: 2 or SEQ ID NO: 4 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for endoglucanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Endoglucanase Activity

A polypeptide having endoglucanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a *Neurospora* polypeptide.

In another aspect, the polypeptide is a *Neurospora tetrasperma, Neurospora crassa, Neurospora africana, Neurospora brevispora, bonaerensis caffera, Neurospora calospora, Neurospora cerealis, Neurospora cratophora, Neurospora dictyophora, Neurospora discreta, Neurospora dodgei, Neurospora himalayensis, Neurospora hippopotama, Neurospora indica, Neurospora intermedia, Neurospora inversa, Neurospora kobi, Neurospora lineolata, Neurospora longispora, Neurospora novoguineensis, Neurospora pannonica, Neurospora pseudocalospora, Neurospora pseudoreticulata, Neurospora reticulate* or *Neurospora sitophila* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 22 to 237 of SEQ ID NO: 2 of at least 99% or 100%. In one aspect, the catalytic domains comprise amino acid sequences that differ by up to 4 amino acids, e.g., 1, 2, 3, or 4 from amino acids 22 to 237 of SEQ ID NO: 2.

The catalytic domain preferably comprises or consists of amino acids 22 to 237 of SEQ ID NO: 2 or an allelic variant thereof; or is a fragment thereof having endoglucanase activity.

In another embodiment, the present invention also relates to catalytic domains encoded by polynucleotides that hybridize under high stringency conditions, or very high stringency conditions (as defined above) with (i) the nucleotides 64 to 764 of SEQ ID NO: 1, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 64 to 764 of SEQ ID NO: 1 or the cDNA sequence thereof of at least 99%, or 100%.

In another embodiment, the present invention also relates to catalytic domain variants of amino acids 22 to 237 of SEQ ID NO: 2 comprising a substitution, deletion, and/or insertion at one or more (e.g., several) positions. In one aspect, the number of amino acid substitutions, deletions and/or insertions introduced into the sequence of amino acids 22 to 237 of SEQ ID NO: 2 is up to 4, e.g., 1, 2, 3 or 4.

Polynucleotides

The present invention also relates to polynucleotides encoding a polypeptide, a catalytic domain, or cellulose binding domain of the present invention, as described herein. In an embodiment, the polynucleotide encoding the polypeptide, catalytic domain, or cellulose binding domain of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Neurospora*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or SEQ ID NO: 3 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoim idazole-succinocarboxam ide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*. The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense,*

*Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Neurospora* cell. In another aspect, the cell is a *Neurospora tetrasperma* or *Neurospora crassa* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Removal or Reduction of Endoglucanase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having endoglucanase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially endoglucanase-free product are of particular interest in the production of eukaryotic polypeptides, in particular fungal proteins such as enzymes. The endoglucanase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from endoglucanase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Signal Peptide

The present invention also relates to a polynucleotide encoding a signal peptide comprising or consisting of amino acids 1 to 21 of SEQ ID NO: 2. The polynucleotides may further comprise a gene encoding a protein, which is operably linked to the signal peptide. The protein is preferably foreign to the signal peptide. In one aspect, the polynucleotide encoding the signal peptide is nucleotides 1 to 63 of SEQ ID NO: 1.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

Enzyme Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Textile Manufacturing Process

The processing of a fabric, such as of a cellulosic material, into material ready for garment manufacture involves several steps: spinning of the fiber into a yarn; construction of woven or knit fabric from the yarn; and subsequent preparation processes, dyeing/printing and finishing operations. Preparation processes are necessary for removing natural and man-induced impurities from fibers and for improving their aesthetic appearance and processability prior to for instance dyeing/printing and finishing. Common preparation processes comprise desizing (for woven goods), scouring, and bleaching, which produce a fabric suitable for dyeing or finishing.

Woven fabric is constructed by weaving "filling" or "weft" yarns between warp yarns stretched in the longitudinal direction on the loom. The warp yarns must be sized before weaving in order to lubricate and protect them from abrasion at the high speed insertion of the filling yarns during weaving. Common size agents are starches (or starch derivatives and modified starches), poly(vinyl alcohol), carboxyl methyl cellulose (i.e. CMC) where starches are dominant. Paraffin, acrylic binders and variety of lubricants are often included in the size mix. The filling yarn can be woven through the warp yarns in a "over one—under the next" fashion (plain weave) or by "over one—under two" (twill) or any other myriad of permutations. Generally, dresses, shirts, pants, sheeting's, towels, draperies, etc. are produced from woven fabric. After the fabric is made, size on the fabric must be removed again (i.e. desizing).

Knitting is forming a fabric by joining together interlocking loops of yarn. As opposed to weaving, which is constructed from two types of yarn and has many "ends", knitted fabric is produced from a single continuous strand of yarn. As with weaving, there are many different ways to loop yarn together and the final fabric properties are dependent both upon the yarn and the type of knit. Underwear, sweaters, socks, sport shirts, sweat shirts, etc. are derived from knit fabrics.

Desizing

Desizing is the degradation and/or removal of sizing compounds from warp yarns in a woven fabric. Starch is usually removed by an enzymatic desizing procedure. In addition, oxidative desizing and chemical desizing with acids or bases are sometimes used.

In some embodiments, the desizing enzyme is an amylolytic enzyme, such as an alpha-amylase, a beta-amylase, a mannanase, a glucoamylase, or a combination thereof.

Suitable alpha and beta-amylases include those of bacterial or fungal origin, as well as chemically or genetically modified mutants and variants of such amylases. Suitable alpha-amylases include alpha-amylases obtainable from *Bacillus* species. Suitable commercial amylases include but are not limited to OPTISIZE® NEXT, OPTISIZE® FLEX and OPTISIZE® COOL (all from Genencor International Inc.), and DURAMYL™, ERMAMYL™, FUNGAMYL™ TERMAMYL™, AQUAZYME™ and BAN™ (all available from Novozymes A/S, Bagsvaerd, Denmark).

Other suitable amylolytic enzymes include the CGTases (cyclodextrin glucanotransferases, EC 2.4.1.19), e.g., those obtained from species of *Bacillus, Thermoanaerobactor* or *Thermoanaero*-bacterium.

Scouring

Scouring is used to remove impurities from the fibers, to swell the fibers and to remove seed coat. It is one of the most critical steps. The main purposes of scouring is to a) uniformly clean the fabric, b) soften the motes and other trashes, c) improve fabric absorbency, d) saponify and solubilize fats, oils, and waxes, and e) minimize immature cotton. Sodium hydroxide scouring at about boiling temperature is the accepted treatment for 100% cotton, while calcium hydroxide and sodium carbonate are less frequently used. Synthetic fibers are scoured at much milder conditions. Surfactant and chelating agents are essential for alkaline scouring. Enzymatic scouring has been introduced, wherein cellulase, hemicellulase, pectinase, lipase, and protease are all reported to have scouring effects.

Bleaching

Bleaching is the destruction of pigmented color and/or colored impurities as well as seed coat fragment removal. It is the most critical chemical treatment since a balance between the degrees of whiteness without fiber damage must be maintained. Bleaching is performed by the use of oxidizing or reducing chemistry. Oxidizing agents can be further subdivided into those that employ or generate: a) hypochlorite ($OCl^-$), b) chloride dioxide ($ClO_2$), and hydroperoxide species. Reducing agents are typical sulfur dioxide, hydrosulfite salts, etc. Enzymatic bleaching using glucose oxidase has been reported. Traditionally, hydrogen peroxide is used in this process.

Printing or Dyeing

Printing or dyeing of textiles is carried out by applying dyes (the noun "dye" and "dyestuff" can be used interchangeable in the context) to the textile by any appropriate method for binding the dyestuff to the fibres in the textiles. The dyeing of textiles is for example carried out by passing the fabric through a concentrated solution of dye, followed by storage of the wet fabric in a vapour tight enclosure to permit time for diffusion and reaction of the dye with the fabric substrate prior to rinsing off un-reacted dye. Alternatively, the dye may be fixed by subsequent steaming of the textile prior to rinsing. Excess soluble dyestuff not bound to the fibres must be removed after dyeing to ensure fastness of the dyed textiles and to prevent unwanted dye transfer during laundering of the textile by the consumer. An enzymatic process for removal of excess dye from dyed fabric with a rinse liquor comprising at least one peroxidase, an oxidase agent and at least one mediator, such as liquor comprising a peroxidase, hydrogen peroxidise and a mediator like 1-hydroxy-benzotriazole is disclosed in WO99/34054.

Biopolishing

As used herein, the term "biopolishing", "bioblasting", "depilling" and "anti-pilling" are interchangeable.

Most cotton fabrics and cotton blend fabrics have a handle appearance that is rather hard and stiff without the application of finishing components. The fabric surface also is not smooth because small fuzzy microfibrils protrude from it. In addition, after a relatively short period of wear, pilling appears on the fabric surface thereby giving it an unappealing, worn look.

Biopolishing is a method to treat cellulosic fabrics during their manufacture by enzymes such as cellulases, which improves fabric quality with respect to "reduced pilling formation". The most important effects of biopolishing can be characterized by less fuzz and pilling, increased gloss/luster, improved fabric handle, increased durable softness and/or improved water absorbency. Biopolishing usually takes place in the wet processing of the manufacture of knitted and woven fabrics or garments. Wet processing comprises such steps as e.g., desizing, scouring, bleaching, washing, dying/printing and finishing. Biopolishing could be performed as a separate step after any of the wetting steps or in combination with any of those wetting steps, such as in combination with catalase bleaching step and/or in combination with dyeing step.

Manufacturing of Denim Fabric

Some dyed fabric such as denim fabric, requires that the yarns are dyed before weaving. For denim fabric, the warp yarns are dyed for example with indigo, and sized before weaving. Preferably the dyeing of the denim yarn is a ring-dyeing. A preferred embodiment of the invention is ring-dyeing of the yarn with a vat dye such as indigo, or an indigo-related dye such as thioindigo, or a sulfur dye, or a direct dye, or a reactive dye, or a naphthol. The yarn may also be dyed with more than one dye, e.g., first with a sulphur dye and then with a vat dye, or vice versa.

Preferably, the yarns undergo scouring and/or bleaching before they are dyed, in order to achieve higher quality of denim fabric. In general, after woven into dyed fabric, such as denim, the dyed fabric or garment proceeds to a desizing stage, preferably followed by a biostoning step and/or a color modification step.

The desizing process as used herein is the same process as mentioned above in the context.

After desizing, the dyed fabric undergoes a biostoning step if a worn look is desired. The biostoning step can be performed with enzymes or pumice stones or both. As used herein, the term "biostoning", "stone washing" and "abrasion" are interchangeable, which means agitating the denim in an aqueous medium containing a mechanical abrasion agent such as pumice, an abrading cellulase or a combination of these, to provide a "stone-washed" look. In all cases, mechanical action is needed to remove the dye, and the treatment is usually carried out in washing machines, like drum washers, belly washers. As a result of uneven dye removal there are contrasts between dyed areas and areas from which dye has been removed, this appears as a localized variation of color density. Treatment with cellulase can completely replace treatment with pumice stones. However, cellulase treatment can also be combined with pumice stone treatment, when it is desired to produce a heavily abraded finish.

Biostoning is generally followed by the third step, after-treatment which generally includes washing and rinsing steps during which detergents, optical brighteners, bleaching agents or softeners may be used.

The method for manufacturing textile of the present invention, by treating textile with an isolated polypeptide having endoglucanase activity as defined in the present invention can be applied to a biostoning process.

In another embodiment, the invention provides a denim manufacturing process, which comprises: a) desizing of the denim fabric; b) biostoning the denim with a polypeptide having endoglucanase activity of the present invention; c) rinsing.

The process of the invention may be carried out at conventional conditions in a washing machine conventionally used for stone-washing, e.g., a washer-extractor, belly washer, etc. The enzyme of the invention should be added in an effective amount.

Process Conditions

Preferably, in the present invention, the method of treating textile with an polypeptide having endoglucanase activity is applied in a biostoning or a biopolishing process. All process conditions below are applicable for both biostoning process and biopolishing process.

It is at present advised that a suitable liquor/textile ratio to be used in the present method may be in the range of from about 20:1 to about 1:1, preferably in the range of from about 15:1 to about 3:1, more preferably in the range of from 15:1 to 5:1 (Volume/weight, ml/g).

In conventional "biostoning" or "biopolishing" processes, the reaction time is usually in the range of from about 10 minutes to about 16 hours. Preferably the reaction time is within the range of from about 20 minutes to about 180 minutes, more preferably the reaction time is within the range of from about 30 minutes to about 120 minutes.

The pH of the reaction medium greatly depends on the enzyme(s) in question. Preferably the process of the invention is carried out at a pH in the range of from about pH 4 to about pH 8, preferably in the range of from about pH 5 to about pH 7.5, or within the range of from about pH 6 to about pH 7.0.

The process of the present invention is able to function at a temperature below 60° C., preferably below 50° C., more preferably below 45° C., more preferably below 40° C., even more preferably below 35° C., even more preferably below 30° C., even more preferably below 25° C.

In some embodiments, the process of the present invention is conducted at the temperature range of 15-65° C., preferably 15-45° C., preferably 20-60° C., preferably 20-55° C., preferably 20-45° C., preferably 20-40° C., more preferably 25-55° C., more preferably 25-50° C., more preferably 25-45° C., more preferably 25-35° C., and even more preferably 30-45° C.

Enzyme dosage greatly depends on the enzyme reaction time and enzyme activity, i.e. a relatively short enzymatic reaction time or low enzymatic activity necessitates a relatively increased enzyme dosage, and vice versa. In general, enzyme dosage may be stipulated in accordance with the reaction time available.

The amount of polypeptide with endoglucanse activity to be used according to the method of the present invention depends on many factors. According to the invention the concentration of the polypeptide of the present invention in the aqueous medium may be from about 0.001 to about 10 milligram (mg) enzyme protein per gram (g) of fabric, preferably 0.02-5 milligram of enzyme protein per gram of fabric, more preferably 0.03-3 milligram of enzyme protein per gram of fabric.

The present invention is further described by the following examples that should not be construed as limiting the scope of the invention.

The present methods and compositions are further described in the following numbered paragraphs.

1. A method for treating textile with a polypeptide having endoglucanase activity selected from the group consisting of:

(a) a polypeptide having at least 90% sequence identity to the mature polypeptide of SEQ ID NO: 2;
(b) a polypeptide encoded by a polynucleotide that hybridizes under high, or very high stringency conditions with (i) the mature polypeptide coding sequence of SEQ ID NO: 1, or (ii) the full-length complementary strand of (i);
(c) a polypeptide encoded by a polynucleotide having at least 90% sequence identity to the mature polypeptide coding sequence of SEQ ID NO: 1;
(d) a variant of the mature polypeptide of SEQ ID NO: 2 comprising a substitution, deletion, and/or insertion at one or more (e.g., several) positions; and
(e) a fragment of the polypeptide of (a), (b), (c), or (d) that has endoglucanase activity.

2. In some embodiments of the method of paragraph 1, wherein the polypeptide having endoglucanase activity has at least 91%, at least 92%, at least 93%, at least 94%, at least 95%, at least 96%, at least 97%, at least 98%, at least 99%, or 100% sequence identity to the mature polypeptide of SEQ ID NO: 2.

3. In some embodiments of the method of paragraph 1, wherein the polypeptide having endoglucanase activity comprises a substitution, deletion, and/or insertion of 10 or 9 or 8 or 7 or 6 or 5 or 4 or 3 or 2 or 1 amino acids of the mature polypeptide of SEQ ID NO: 2.

4. In some embodiments of the method of any of the paragraphs 1-3, wherein the polypeptide having endoglucanase activity is obtained from *Neurospora*, especially *Neurospora tetrasperma* or *Neurospora crassa*.

5. In some embodiments of the method of any of the paragraphs 1-4, comprising or consisting of SEQ ID NO: 2 or SEQ ID NO: 4, or the mature polypeptide of SEQ ID NO: 2 or SEQ ID NO: 4.

6. In some embodiments of the method of any of the preceding paragraphs, wherein the mature polypeptide is amino acids 22 to 237 of SEQ ID NO: 2 or amino acids 22 to 237 of SEQ ID NO: 4.

7. In some embodiments of the method of any of the preceding paragraphs, wherein the method is conducted under a temperature range of 15-65° C., preferably 20-60° C., more preferably 25-55° C., more preferably 25-50° C., and even more preferably 30-45° C.

8. In some embodiments of the method of any of the preceding paragraphs, wherein the method is conducted under pH 4 to about pH 8, preferably in the range of about pH 5 to about pH 7.5, or within the range of about pH 6 to about pH 7.

9. In some embodiments of the method of any of the preceding paragraphs, wherein the method is applied in a biopolishing process.

10. In some embodiments of the method of any of the preceding paragraphs, wherein the method is applied in a biostoning process.

11. In some embodiments of the method of any of the preceding paragraphs, wherein the treating textile is manufacturing the textile.

12. A polypeptide having endoglucanase activity selected from the group consisting of:
(a) a polypeptide having at least 99% sequence identity to the mature polypeptide of SEQ ID NO: 2;
(b) a polypeptide encoded by a polynucleotide that hybridizes under high, or very high stringency conditions with (i) the mature polypeptide coding sequence of SEQ ID NO: 1, or (ii) the full-length complementary strand of (i);
(c) a polypeptide encoded by a polynucleotide having at least 99% sequence identity to the mature polypeptide coding sequence of SEQ ID NO: 1;
(d) a variant of the mature polypeptide of SEQ ID NO: 2 comprising a substitution, deletion, and/or insertion at one or more (e.g., several) positions; and
(e) a fragment of the polypeptide of (a), (b), (c), or (d) that has endoglucanase activity.

13. In some embodiments of the method of paragraph 12, having at least 99% or 100% sequence identity to the mature polypeptide of SEQ ID NO: 2.

14. In some embodiments of the method of paragraph 12 or 13, comprising a substitution, deletion, and/or insertion of 5 or 4 or 3 or 2 or 1 amino acids of the mature polypeptide of SEQ ID NO: 2.

15. In some embodiments of the method of any of paragraphs 12-14, comprising or consisting of SEQ ID NO: 2, or the mature polypeptide of SEQ ID NO: 2.

16. In some embodiments of the method of any of the paragraphs 12-15, wherein the mature polypeptide is amino acids 22 to 237 of SEQ ID NO: 2.

17. A polypeptide comprising a catalytic domain selected from the group consisting of:
(a) a catalytic domain having at least 99% sequence identity to amino acids 22 to 237 of SEQ ID NO: 2;
(b) a catalytic domain encoded by a polynucleotide that hybridizes under very high stringency conditions with (i) nucleotides 64 to 764 of SEQ ID NO: 1, (ii) the cDNA sequence thereof, or (iii) the full-length complement of (i) or (ii);
(c) a catalytic domain encoded by a polynucleotide having at least 99% sequence identity to nucleotides 64 to 764 of SEQ ID NO: 1 or the cDNA sequence thereof;
(d) a variant of amino acids 22 to 237 of SEQ ID NO: 2 comprising a substitution, deletion, and/or insertion at one or more (e.g., several) positions; and
(e) a fragment of the catalytic domain of (a), (b), (c), or (d) that has endoglucanase activity.

18. In some embodiments of the method of any of paragraphs 12-17, which is obtained from *Neurospora*, especially *Neurospora tetrasperma* or *Neurospora crassa*.

19. A composition comprising the polypeptide of any of paragraphs 12-18.

20. A polynucleotide encoding the polypeptide of any of paragraphs 12-18.

21. A nucleic acid construct or expression vector comprising the polynucleotide of paragraph 20 operably linked to one or more control sequences that direct the production of the polypeptide in an expression host.

22. A recombinant host cell comprising the polynucleotide of paragraph 20 operably linked to one or more control sequences that direct the production of the polypeptide.

23. A method of producing the polypeptide of any of paragraphs 12-18, comprising cultivating a cell, which in its wild-type form produces the polypeptide, under conditions conducive for production of the polypeptide.

24. The method of paragraph 23, further comprising recovering the polypeptide.

25. A method of producing a polypeptide having endoglucanase activity, comprising cultivating the host cell of paragraph 22 under conditions conducive for production of the polypeptide.

26. The method of paragraph 25, further comprising recovering the polypeptide.

27. A transgenic plant, plant part or plant cell transformed with a polynucleotide encoding the polypeptide of any of paragraphs 12-18.

28. A method of producing a polypeptide having endoglucanase activity, comprising cultivating the transgenic plant or plant cell of paragraph 27 under conditions conducive for production of the polypeptide.

29. The method of paragraph 28, further comprising recovering the polypeptide.

30. A method of producing a mutant of a parent cell, comprising inactivating a polynucleotide encoding the polypeptide of any of paragraphs 12-18, which results in the mutant producing less of the polypeptide than the parent cell.

31. A mutant cell produced by the method of paragraph 30.

32. The mutant cell of paragraph 31, further comprising a gene encoding a native or heterologous protein.

33. A method of producing a protein, comprising cultivating the mutant cell of paragraph 31 or 32 under conditions conducive for production of the protein.

34. The method of paragraph 33, further comprising recovering the protein.

35. A double-stranded inhibitory RNA (dsRNA) molecule comprising a subsequence of the polynucleotide of paragraph 20, wherein optionally the dsRNA is an siRNA or an miRNA molecule.

36. The double-stranded inhibitory RNA (dsRNA) molecule of paragraph 35, which is about 15, 16, 17, 18, 19, 20, 21, 22, 23, 24, 25 or more duplex nucleotides in length.

37. A method of inhibiting the expression of a polypeptide having endoglucanase activity in a cell, comprising administering to the cell or expressing in the cell the double-stranded inhibitory RNA (dsRNA) molecule of paragraph 35 or 36.

38. A cell produced by the method of paragraph 37.

39. The cell of paragraph 38, further comprising a gene encoding a native or heterologous protein.

40. A method of producing a protein, comprising cultivating the cell of paragraph 38 or 39 under conditions conducive for production of the protein.

41. The method of paragraph 40, further comprising recovering the protein.

42. A polynucleotide encoding a signal peptide comprising or consisting of amino acids 1 to 21 of SEQ ID NO: 2.

43. A nucleic acid construct or expression vector comprising a gene encoding a protein operably linked to the polynucleotide of paragraph 42, wherein the gene is foreign to the polynucleotide encoding the signal peptide.

44. A recombinant host cell comprising a gene encoding a protein operably linked to the polynucleotide of paragraph 42, wherein the gene is foreign to the polynucleotide encoding the signal peptide.

45. A method of producing a protein, comprising cultivating a recombinant host cell comprising a gene encoding a protein operably linked to the polynucleotide of paragraph 42, wherein the gene is foreign to the polynucleotide encoding the signal peptide, under conditions conducive for production of the protein.

46. The method of paragraph 45, further comprising recovering the protein.

47. A whole broth formulation or cell culture composition comprising a polypeptide of any of paragraphs 12-18.

EXAMPLES

Materials

Chemicals used as buffers and substrates were commercial products of at least reagent grade.

Strains

*Neurospora tetrasperma* strain NRRL11265 was used as the source of the family GH45 endoglucanase gene.

*Aspergillus oryzae* MT3568 strain was used for heterologous expression of the family GH45 gene encoding a polypeptide having homology with polypeptides with endoglucanase activity. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

Media

DAP-4C-1 media was composed of 0.5 g yeast extract, 10 g maltose, 20 g dextrose, 11 g magnesium sulphate heptahydrate, 1 g dipotassium phosphate, 2 g citric acid monohydrate, 5.2 g potassium phosphate tribasic monohydrate, 1 ml Dowfax 63N10 (antifoaming agent), 2.5 g calcium carbonate, supplemented with 1 ml KU6 metal solution, and deionised water to 1000 ml.

KU6 metal solution was composed of 6.8 g $ZnCl_2$, 2.5 g $CuSO_4.5H_2O$, 0.13 g $NiCl_2$, 13.9 g $FeSO4.7H_2O$, 8.45 g $MnSO_4.H_2O$, 3 g $C_6H_8O_7.H_2O$, and deionized water to 1000 ml.

PDA plates were composed of 39 g Potato Dextrose Agar and deionized water to 1000 ml.

LB plates were composed of 10 g of Bacto-Tryptone, 5 g of yeast extract, 10 g of sodium chloride, 15 g of Bacto-agar, and deionized water to 1000 ml.

LB medium was composed of 10 g of Bacto-Tryptone, 5 g of yeast extract, and 10 g of sodium chloride, and deionized water to 1000 ml.

COVE-Sucrose-T plates were composed of 342 g of sucrose, 20 g of agar powder, 20 ml of COVE salt solution, and deionised water to 1000 ml. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 µl/500 ml) was added.

COVE-N-Agar tubes were composed of 218 g Sorbitol, 10 g Dextrose, 2.02 g $KNO_3$, 25 g Agar, 50 ml Cove salt solution, and deionised water up to 1000 ml.

COVE salt solution was composed of 26 g of $MgSO_4.7H_2O$, 26 g of KCL, 26 g of $KH_2PO_4$, 50 ml of COVE trace metal solution, and deionised water to 1000 ml.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1000 ml.

MDU2BP medium contains per liter 45 g maltose, 1 g $MgSO_4.7H_2O$, 1 g NaCl, 2 g $K_2SO_4$, 12 g $KH_2PO_4$, 7 g yeast extract, 2 g urea and 0.5 ml AMG trace metals. The medium is titrated to pH 5.0 with NaOH and filter sterilized.

AMG trace metals were composed of per liter 14.3 g $ZnSO_4.7H_2O$, 2.5 g $CuSO_4.5H_2O$, 0.5 g $NiCl_2$, 13.8 g $FeSO_4$, 8.5 g $MnSO_4$, 3.0 g citric acid.

YEG medium contains per liter 5 g yeast extract and 20 g dextrose and is sterilized by autoclaving.

TE buffer contains 10 mM Tris-HCl and 0.1 mM EDTA pH 8.0.

pH 5.0 buffer with 50 mM acetate: 2.873 g sodium acetate and 0.901 g acetic acid were dissolved in 1 L de-ionized water;

pH 6.5 buffer with 50 mM phosphate: 5.642 g disodium hydrogen phosphate dodecahydrate ($Na_2HPO_4.12H_2O$) and 5.344 g sodium dihydrogen phosphate dehydrate ($NaH_2PO_4.2H_2O$) were dissolved in 1 L de-ionized water;

pH 7.5 buffer with 50 mM phosphate: 15.045 g disodium hydrogen phosphate dodecahydrate ($Na_2HPO_4.12H_2O$) and 1.248 g sodium dihydrogen phosphate dehydrate (NaH$_2$PO$_4$.2H$_2$O) were dissolved in 1 L de-ionized water;

pH 8.5 buffer with 50 mM phosphate: 17.607 g disodium hydrogen phosphate dodecahydrate (Na$_2$HPO$_4$.12H$_2$O) and 0.116 g potassium dihydrogen phosphate (KH$_2$PO$_4$) were dissolved in 1 L de-ionized water.

Enzymes

Biotouch XC 300® (a neutral cellulase product, commercially available from AB Enzymes, described as SEQ ID NO:13 Geomyces pannorum RF6293 Cel45 in WO2010/076388)

Fabrics

Cotton interlock: 40S, bleached, HM-A0008, available from HM Cotton Co., Ltd, Guangzhou, China.

Denim: batch No. L001, 7*7/76*42, 12 oz., available from Hangzhou Yimei Co., Ltd, China.

Method

Weight Loss Determination

The swatches were placed in the conditioned room (65%+/−5% humidity, 20+/−1° C.) for 24 hours before they were numbered, weighed by the analytical balance (for samples below 100 g) or a precision balance (for samples over 100 g) and recorded. After treatment, all samples were tumbled dried (AEG, LAVATHERM 37700, Germany) for 1 hour and conditioned for 24 hours in the conditioned room mentioned as above. For each sample, the weight loss was defined as below:

$$\text{Weight loss \%} = \frac{(\text{weight before-weight after}) * 100}{\text{weight before treatment}}$$

Pilling Notes Test

Fabrics including treated and untreated which had been pre-conditioned in norm climate (65% humidity, 21° C.) for at least 24 hours were tested for the pilling notes with Nu-Martindale Tester (James H. Heal Co. Ltd, England), with untreated fabrics of the same type as the abraded fabrics. A standard pilling test (Swiss Norm (SN) 198525) was carried out after 2000 Revolutions by marking from 1-5, with the meaning defined as below, where 1 shows poor anti-pilling and 5 shows excellent anti-pilling property. Thus the higher the Martindale pilling notes score the more effective the endo-glucanase biopolishing treatment.

Note 5: No pilling
Note 4: Slight Pilling
Note 3: Moderate Pilling
Note 2: Distinct Pilling
Note 1: Heavy Pilling
½, ¼ notes are allowed To make the test result more reliable, 3 separate readings were carried out by different persons for each sample, and the average of the 3 readings was adopted as the final result of pilling notes.

Color Measurement for Denim

The abrasion level and backstaining level of the denim samples were determined by measuring the reflectance with pre-calibrated DataColor SF450X, alternatively an equivalent apparatus can be used. Four readings were taken for each sample, and the average of the readings were used. The abrasion level was evaluated with the index CIE L* on the blue side (front side) of the sample, and the backstaining level was evaluated with the index CIE b* on the back side of the sample.

L* indicates the change in white/black on a scale from 0 to 100, and a decrease in L* means an increase in black colour (decrease in white colour) and an increase in L* means an increase in white colour (decrease in black colour). Delta L* unit=L* of the swatch treated with a certain celllulase −L* of the swatch before cellulase treatment. The larger the Delta L* unit is the higher is the denim abrasion level, e.g. a Delta L* unit of 4 has higher abrasion level than Delta L* unit of 3.

b* indicates the change in blue/yellow, and a decrease in b* means an increase in blue colour (decrease in yellow colour), and an increase in b* means an increase in yellow colour (decrease in blue colour). Delta b* units=b* of the swatch treated with a certain celllulase −b* of the swatch before cellulase treatment. A larger Delta b* unit corresponds to a lower backstaining level, e.g. a Delta b* unit of −1.5 has lower backstaining level than the Delta b* unit of −2.5.

Protein Content

The enzyme protein in an enzyme product can be measured with BCA™ Protein Assay Kit (product number 23225, commercial available from Thermo Fisher Scientific Inc.) according to the product manual.

Example 1: Cloning of a Family GH45 Gene from *Neurospora tetrasperma*

A set of cloning primers (SEQ ID NO: 5, and SEQ ID NO: 6) was designed to PCR— amplify the gene encoding for SWISSPROT: G4V0S1. A 5' tag for InFusion cloning in our expression vector was added to the cloning primers according to the protocol described in the InFusion HD EcoDry Cloning Kit (Cat. 639691) (Clontech Laboratories, Inc., Mountain View, Calif., USA) to fit cloning in the expression vector pDAu109 (WO 2005042735).

```
Forward primer:
                                    (SEQ ID NO: 5)
ACACAACTGGGGATCCACCATGCGCTCCTCCACTGTTCTGC Reverse primer:
                                    (SEQ ID NO: 6)
AGATCTCGAGAAGCTTAGGCACACTGGTGGTAATAATCGTTGA
```

The *N. tetrasperma* endoglucanase gene was amplified by PCR using the forward and reverse cloning primers described above (SEQ ID NO: 5 and 6) with *Neurospora tetrasperma* strain NRRL11265 genomic DNA, previously prepared from mycelium grown on PDA plates with the MPBIO's kit (FastDNA Spin kit for soil, Cat. 116560-200). The PCR was composed of 1 μl of genomic DNA, 2.5 μl of cloning primer forward (10 μM), 2.5 μl of cloning primer reverse (10 μM), 10 μl of 5×HF buffer (Finnzymes Oy, Espoo, Finland), 1.6 μl of 50 mM MgCl$_2$, 2 μl of 10 mM dNTP, 0.5 μl of PHUSION® DNA polymerase (Finnzymes Oy, Espoo, Finland), and PCR-grade water to 50 μl. Primers SEQ ID NO: 5 and SEQ ID NO: 6 were used on genomic DNA from *N. tetrasperma*. The amplification reaction was performed using a DYAD® Thermal Cycler (M.J. Research Inc. South San Francisco, Calif., USA) programmed for 2 minutes at 98° C. followed by 19 touchdown cycles each at 98° C. for 15 seconds, 70° C. (−1° C./cycle) for 30 seconds, and 72° C. for 2 minutes and 30 seconds; and 25 cycles each at 98° C. for 15 seconds, 60° C. for 30 seconds, 72° C. for 2 minutes and 30 seconds, and finally an extension of 5 minutes at 72° C.

The reaction products were isolated on 1.0% agarose gel electrophoresis using TAE buffer where an approximately 0.9 to 0.95 kb PCR band was excised from the gel and purified using a GFX® PCR DNA and Gel Band Purification Kit (GE Healthcare, HiHerød, Denmark) according to manufacturer's instructions. DNA corresponding to the *N. tetrasperma* endoglucanase gene was cloned into the expression vector pDAu109 (WO 2005042735) previously linearized with Bam HI and Hind III, using an IN-FUSION™ Dry-Down PCR Cloning Kit (Cat. 639691) (Clontech Laboratories, Inc., Mountain View, Calif., USA) according to the manufacturer's instructions.

A 2.5 µl volume of the diluted ligation mixture was used to transform *E. coli* TOP10 chemically competent cells (Invitrogen, Carlsbad, Calif., USA). Three colonies were selected on LB agar plates containing 100 µg of ampicillin per ml and cultivated overnight in 3 ml of LB medium supplemented with 100 µg of ampicillin per ml. Plasmid DNA was purified using a Qiagen Spin Miniprep kit (Cat. 27106) (QIAGEN GmbH, Hilden, Germany) according to the manufacturer's instructions. The *N. tetrasperma* gene sequence was verified by Sanger sequencing before heterologous expression. The plasmid designated as 001-8#1 (containing gene SEQ ID NO: 1) was selected for protoplast transformation and heterologous expression of its encoded endoglucanase in an *Aspergillus oryzae* host cell MT3568.

Example 2: Characterization of the *Neurospora tetrasperma* Genomic DNA Encoding a Family GH45 Polypeptide The genomic DNA sequence (SEQ ID NO: 1) and deduced amino acid sequence (SEQ ID NO: 2) of the *Neurospora tetrasperma* endoglucanase gene is shown below. The coding sequence of SEQ ID NO: 1 is 935 bp including the stop codon with one predicted intron (339.0.391). The encoded predicted protein is 293 amino acids. Using the SignalP program (Nielsen et al., 1997, *Protein Engineering* 10: 1-6), a signal peptide of 21 residues was predicted. Using PEPSTATS from EMBOSS package (Rice et al., 2000, *Trends in Genetics* 16: 276-277) a mature protein of 272 amino acids was predicted with a molecular mass of 28 kDa and an isoelectric point of 6.9.

A comparative pairwise global alignment of amino acid sequence (SEQ ID NO: 2) was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *N. tetrasperma* gDNA encoding a family GH45 polypeptide having homology to proteins with endoglucanase activity shares 98.9% identity (excluding gaps) to the deduced amino acid sequence of an endoglucanase from *N. tetrasperma* (Uniprot: G4V0S1).

Example 3: Transformation of *Aspergillus oryzae* with the Gene Encoding an Endoglucanase from *Neurospora tetrasperma* and Selection of the Best Transformants Protoplasts of *Aspergillus oryzae* MT3568 were prepared according to WO 95/002043. One hundred µl of protoplasts were mixed with 2.5-15 µg of the plasmid 001-8#1 (prepared in Example 1) and 250 µl of 60% PEG 4000 (Applichem, Darmstadt, Germany) (polyethylene glycol, molecular weight 4,000), 10 mM $CaCl_2$, and 10 mM Tris-HCl pH 7.5 and gently mixed. The mixture was incubated at 37° C. for 30 minutes and the protoplasts were spread onto COVE plates for selection. After incubation for 4-7 days at 37° C. spores of eight transformants were inoculated into 0.5 ml of DAP-4C-1 medium supplemented lactic acid and with diammonium phosphate in 96 deep well plates. After 4 days cultivation at 30° C., the culture broths were analyzed by SDS-PAGE using Novex® 4-20% Tris-Glycine Gel (Invitrogen Corporation, Carlsbad, Calif., USA) to identify the transformants producing the largest amount of recombinant endoglucanase from *N. tetrasperma*.

Spores of the best transformant were spread on COVE-Sucrose-T plates containing 0.01% TRITON® X-100 in order to isolate single colonies. The spreading was repeated twice in total on COVE-Sucrose-T plates, and then a single colony was spread on a COVE-N-Agar tube until sporulation.

Example 4: Fermentation of *Aspergillus oryzae* Transformed with the Gene Encoding an Endoglucanase from *Neurospora tetrasperma*

150 ml of DAP-4C-1 media supplemented with 5 ml of 20% lactic acid and 3.5 ml of 50% diammonium phosphate and spores from the best transformants were cultivated in shake flasks during 4 days at a temperature of 30° C. under 100 rpm agitation. Culture broth was harvested by filtration using a 0.2 µm filter device.

Example 5: Purification of Recombinant *Neurospora tetrasperma* Endoglucanase $(NH_4)_2SO_4$ was added to the culture broth of the recombinant *Aspergillus oryzae* (transformant prepared in Example 3), the final concentration of $(NH_4)_2SO_4$ was 1.2M. The solution was filtered through a 0.45 mm filter and applied to a 40 ml Phenyl Sepharose 6 Fast Flow column (GE) equilibrated using the equilibration buffer consisting of 20 mM Tris-HCl, pH 7.0 supplemented with 1.2 M $(NH_4)_2SO_4$, the protein was eluted with a linear $(NH_4)_2SO_4$ gradient (1.2-0 M). Fractions were evaluated by SDS-PAGE (NP0336BOX, NUPAGE 4-12% BT GEL 1.5MM15W). Fractions containing a band of approximately 28 kDa were pooled. Then the pooled solution was concentrated by ultrafiltration.

Example 6: Identification of a Glycosyl Hydrolase Family GH45 Gene in the Genomic Sequence of *Neurospora crassa*

A tblastn search (Altschul et al., 1997, *Nucleic Acids Res.* 25: 3389-3402) of the *Neurospora crassa* genome sequence (The Broad Institute, Cambridge, Mass., USA) was carried out using as query the GH45 endoglucanase V protein sequence from *Humicola insolens* (GeneSeqP accession number AEB00296). One gene was identified as a putative Family GH45 homolog based upon a high degree of similarity to the query sequences at the amino acid level. This genomic region of 935 bp was chosen for cloning.

Example 7: *Neurospora crassa* Genomic DNA Extraction

A *Neurospora crassa* strain FGSC 2489 (obtained from the Fungal Genetics Stock Center, Kansas Cit, Mo.) was grown in 100 mL YEG medium for 2 days at 34° C. in a shake flask. Mycelia were harvested on a glass fiber filter and frozen in liquid nitrogen. Frozen mycelia were ground, by mortar and pestle, to a fine powder. Approximately $\frac{1}{4}^{th}$ of the powder was suspended in 15 mL of TE buffer to which was added 4 mL of 0.1 M CAPS-NaOH buffer, pH 11.0, and 1.0 mL of 10% lithium dodecyl sulfate. The suspension was incubated at 60° C. for 60 min with periodic mixing by inversion. To this was added 20 mL of neutralized phenol: chloroform: isoamyl alcohol (25:24:1 v/v/v), and the tube was mixed by inversion on a rotating wheel for 60 min. After centrifugation at 2500 rpm for 5 min, the aqueous phase was removed and re-extracted with phenol:chloroform:isoamyl alcohol in the same fashion. The aqueous phase was brought to 2.5 M ammonium acetate by addition of one-third volume of 10 M ammonium acetate, and frozen on dry ice. After thawing, the suspension was centrifuged at 15,000×g for 20 min, the solution decanted off, and nucleic acids precipitated by addition of 0.7 volumes of isopropanol. After centrifugation at 15,000×g for 20 min, the solution was decanted off and the pellet washed twice with 70% ethanol and air dried. The pellet was dissolved in 1.0 mL 0.1×TE. RNase A (QIAGEN Inc., Valencia, Calif., USA) was added to 100 μg/mL and the solution incubated for 30 min at room temperature. Nucleic acids were precipitated by addition of ¼$^{th}$ volume 10 M ammonium acetate and 2 volumes of 95% ethanol. After centrifugation at 15,000×g for 20 min, the supernatant was removed and the pellet washed twice with 70% ethanol and air dried. The DNA was dissolved in 0.75 mL 0.1×TE.

Example 8: Construction of an *Aspergillus oryzae* Expression Vector for the *Neurospora crassa* Endoglucanase Gene Two synthetic oligonucleotide primers shown below were designed to PCR amplify the *Neurospora crassa* endoglucanase gene from the genomic DNA. An IN-FUSION® Cloning Kit (BD Biosciences, Palo Alto, Calif., USA) was used to clone the fragment directly into the expression vector pAILo2 (described in WO 2005/074647), without the need for restriction digestion and ligation.

```
Forward primer:
                                        (SEQ ID NO: 7)
5'-ACTGGATTTACCATGCGCTCCTCCACTATTCTGCAAA-3'

Reverse primer:
                                        (SEQ ID NO: 8)
5'-TCACCTCTAGTTAATCAGGCACACTGATGGTAAT-3'
```

The underlined letters represent coding sequence. The remaining sequence is homologous to the insertion sites of pAILo2.

Fifty picomoles of each of the primers above were used in a PCR reaction containing 5.0 μL of *Neurospora crassa* genomic DNA (prepared as described in Example 7), 1× Pfx Amplification Buffer (Invitrogen, Carlsbad, Calif., USA), 8 microliter (μl) of 10 mM blend of dATP, dTTP, dGTP, and dCTP, 3.75 units of Platinum Pfx DNA Polymerase (Invitrogen, Carlsbad, Calif.), and 3 μl of 50 mM MgSO$_4$ in a final volume of 150 μl. This was divided into 3×50 μl aliquots and the amplification was performed using a Robocycler Gradient 40 (Stratagene, La Jolla, Calif., USA) programmed for one cycle at 94° C. for 3 minutes; and 30 cycles each at 94° C. for 30 seconds, 50, 53, or 57° C. for 30 seconds, and 68° C. for 75 seconds. The heat block was then held at 72° C. for 10 minutes followed by a 4° C. soak cycle.

The reaction products were isolated by 0.8% agarose gel electrophoresis using TAE buffer (40 mM Tris base, 20 mM sodium acetate, 1 mM disodium EDTA) where an approximately 950 bp product band was excised from 3 lanes of the gel (representing the 3 different PCR annealing temperatures) and purified using an Eppendorf Perfectprep® Gel Cleanup kit (Brinkmann Instruments, Inc., Westbury, N.Y., USA) according to the manufacturer's instructions.

The fragment was then cloned into pAILo2 using an IN-FUSION® Cloning Kit. The vector was digested with Nco I and Pac I. The fragment was purified by gel electrophoresis as above and a QIAQUICK® Gel Purification Kit (QIAGEN Inc., Valencia, Calif., USA). The gene fragment and the digested vector were combined together in a reaction resulting in the expression plasmid pPH45, in which transcription of the *Neurospora crassa* endoglucanase gene was under the control of the NA2-tpi promoter (a hybrid of the promoters from the genes for *Aspergillus niger* neutral alpha-amylase and *Aspergillus oryzae* triose phosphate isomerase). The recombination reaction (20 μl) was composed of 1×IN-FUSION® Buffer (BD Biosciences, Palo Alto, Calif., USA), 1×BSA (BD Biosciences, Palo Alto, Calif., USA), 1 μl of IN-FUSION® enzyme (diluted 1:10) (BD Biosciences, Palo Alto, Calif., USA), 166 ng of pAILo2 digested with Nco I and Pac I, and 170 ng of the *Neurospora crassa* endoglucanase purified PCR product. The reaction was incubated at room temperature for 30 minutes and 3 μl of the reaction product was transformed into *E. coli* XL1-Blue Competent cells (Stratagene, La Jolla, Calif., USA) according to the manufacturer's instructions. An *E. coli* transformant containing plasmid pPH45 was identified by restriction enzyme digestion and plasmid DNA was prepared using a BIOROBOT® 9600 (QIAGEN Inc., Valencia, Calif., USA).

Example 9: Characterization of the *Neurospora crassa* Genomic Sequence Encoding Cel45A DNA sequencing of the 935 bp insert in pPH45 was performed with a Perkin-Elmer Applied Biosystems Model 377 XL Automated DNA Sequencer using dye-terminator chemistry (Giesecke et al., 1992, supra) and primer walking strategy. The following vector specific primers were used for sequencing:

```
pAllo2 5' Seq:
                                        (SEQ ID NO: 9)
    5' TGTCCCTTGTCGATGCG 3' pAllo2 3' Seq:
                                        (SEQ ID NO: 10)
    5' CACATGACTTGGCTTCC 3'
```

Nucleotide sequence data were scrutinized for quality and all sequences were compared to each other with assistance of PHRED/PHRAP software (University of Washington, Seattle, Wash., USA). The sequence was a 100% match to the *Neurospora crassa* strain FGSC 2489 genome sequence determined by the *Neurospora crassa* sequencing project and available at the Broad Institute (Cambridge, Mass., USA)

A gene model for the *Neurospora crassa* sequence was constructed based on similarity of the encoded protein to a *Humicola insolens* endoglucanase V protein (GeneSeqP Accession Number AEB00296). The nucleotide sequence and deduced amino acid sequence are SEQ ID NO: 3 and SEQ ID NO: 4, respectively. The genomic fragment encodes a polypeptide of 293 amino acids, interrupted by one intron of 53 bp (nucleotides 339 to 391). Using the SignalP software program (Nielsen et al., 1997, *Protein Engineering* 10: 1-6), a signal peptide of 21 residues was predicted.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Neurospora crassa* gene encoding the endoglucanase mature polypeptide shared 100% identity to the deduced amino acid sequence of the *Neurospora crassa* B19A17.010 protein (UniProt Accession Number Q872Q1).

Example 10: Expression of the *Neurospora crassa* Genomic DNA Encoding Endoglucanase in *Aspergillus oryzae* JaL250

*Aspergillus oryzae* JaL250 protoplasts were prepared according to the method of Christensen et al., 1988, *Bio/Technology* 6: 1419-1422. Six µg of pPH45 was used to transform *Aspergillus oryzae* JaL250. Eight transformants were isolated to individual PDA plates.

Confluent PDA plates of the transformants were each washed with 8 ml of 0.01% TWEEN® 20, 0.7 M KCl and the spores were each collected. Two ml of each spore stock was added to 25 ml of MDU2BP medium in 125-mL flasks and incubated at 34° C. and 200 rpm. After 4 days of incubation, 10 µl of supernatant from each flask was analyzed using a Novex NuPAGE®, 4-12% gradient SDS-PAGE gel (Life Technologies, Grand Island, N.Y.) according to the manufacturer's instructions. SDS-PAGE profiles of the cultures showed that all transformants had a new band of approximately 32 kDa. The transformant with the highest expression level was named Jal250PaHa45.

Example 11: Purification of Recombinant *Neurospora crassa* Endoglucanase $(NH_4)_2SO_4$ was added to the culture broth of the recombinant *Aspergillus oryzae* transformant (prepared in Example 10), the final concentration of $(NH_4)_2SO_4$ was 1.2M. The solution was filtered through a 0.45 mm filter and applied to a 40 ml Phenyl Sepharose 6 Fast Flow column (GE) equilibrated using the equilibration buffer consisting of 20 mM Tris-HCl, pH 7.0 supplemented with 1.2 M $(NH_4)_2SO_4$, the protein was eluted with a linear $(NH_4)_2SO_4$ gradient (1.2-0 M). Fractions were evaluated by SDS-PAGE (NP0336BOX, NUPAGE 4-12% BT GEL 1.5MM15W). Fractions containing a band of approximately 29 kDa were pooled. Then the pooled solution was concentrated by ultrafiltration.

Example 12: Purification of Cellulase from Biotouch XC300

A 100 ml volume of filtered Biotouch XC300 was precipitated with ammonium sulfate (80% saturation), re-dissolved in 40 ml of 20 mM Tris-HCl pH 7.0, dialyzed against the same buffer, and filtered through a 0.45 µm filter. The final volume was 80 ml. The solution was applied to a 40 ml Q SEPHAROSE® Fast Flow column equilibrated with 20 mM Tris-HCl pH 7.0. Proteins were eluted with a linear 0-0.5 M NaCl gradient. Fractions unbound to the column were collected and further purified using a 40 ml Phenyl SEPHAROSE® 6 Fast Flow column (GE Healthcare, Buckinghamshire, UK) with a linear 1.2-0 M $(NH_4)_2SO_4$ gradient. Fractions were analyzed by SDS-PAGE using a NUPAGE® NOVEX® 4-12% Bis-Tris Gel with 50 mM MES. The resulting gel was stained with INSTANT-BLUE™. Fractions containing a band at approximately 40 kDa were pooled. Then the pooled solution was concentrated by ultrafiltration.

Example 13: Endoglucanase Activity Assay 0.2% AZCL-HE-cellulose (Megazyme, I-AZCEL) was suspended in 20 mM Bis-Tris buffer of pH 6.0 with addition of 0.01% Triton X-100 by gentle stirring, which was used as a substrate. Then 120 microliter substrate and 30 microliter enzyme sample of 1 mg/ml prepared according to Example 5, 11 and 12 respectively were mixed in a Microtiter plate and placed on ice before reaction. The assay was initiated by transferring the Microtiter plate to an Eppendorf thermomixer, which was set to the assay temperature of 50° C. The plate was incubated for 20 minutes on the Eppendorf thermomixer at its shaking rate 700 rpm for Microtiter plate. The incubation was stopped by transferring the plate back to the ice bath. Then the plate was centrifuged in an ice cold centrifuge for 5 minutes and 100 microliter supernatant was transferred to a microtiter plate. $OD_{595}$ was read as a measure of endoglucanase activity. All reactions were done with triplicate and a buffer blind without adding any enzyme was included in the assay.

If $OD_{595}$ value of the enzyme sample minus $OD_{595}$ value of the blind is above 0, the enzyme is defined as the enzyme having endoglucanase activity.

$OD_{595}$ value of the *Neurospora tetrasperma* GH45 endoglucanase sample tested in this example minus $OD_{595}$ of the blind was above 0, which shows the *Neurospora tetrasperma* GH45 endoglucanase in the present invention has the endoglucanase activity.

$OD_{595}$ value of the *Neurospora crassa* GH45 endoglucanase sample tested in this example minus $OD_{595}$ of the blind was above 0, which shows the *Neurospora crassa* GH45 endoglucanase in the present invention has the endoglucanase activity.

$OD_{595}$ value of the Biotouch XC300 endoglucanase sample tested in this example minus $OD_{595}$ of the blind was above 0, which shows the Biotouch XC300 endoglucanase in the present invention has the endoglucanase activity.

Example 14: Biopolishing with *Neurospora crassa* GH45, *Neurospora tetrasperma* GH45 and Biotouch XC 300 in Launder-O-Meter

*Neurospora tetrasperma* GH45 endoglucanase (abbreviated as Nt Cel45, mature peptide of SEQ ID NO: 2), *Neurospora crassa* GH45 endoglucanase (abbreviated as Nc Cel45, mature peptide of SEQ ID NO: 4) and the protein from commercially available product Biotouch XC300 were evaluated for biopolishing after purification as described in Example 5, 11 and 12 respectively.

Cotton fabric swatches were cut into about 16 cm*16 cm (about 5 grams each). The swatches were placed in the conditioned room (65% humidity, 21° C.) for 24 hours before they were numbered, weighed by the analytical balance and recorded. The biopolishing was conducted with a Launder-O-meter. Two conditioned swatches and 20 big steel balls (total weight of 220 grams) were placed in each beaker to supply the mechanical aids. The beaker was filled with enzymes according to Table 1 and buffers prepared as described in media part to a total volume of around 100 ml, which could get a liquid to fabric ratio of about 10:1 (v/w, ml/g).

The Launder-O-Meter (LOM) machine was started after the required program was chosen, and it would hold when the temperature reached the pre-set temperature, e.g. 35° C. or 55° C. Each beaker was fitted with a lid lined with 2 neoprin gaskets and close tightly with the metal clamping device. The beakers were loaded into the preheated LOM. Metal racks were used to accommodate and secure 5 beakers, in the vertical position, in each of the 4 drum positions. The LOM lid was closed and the washing program was continued and the timing was initiated. After the treatment with cellulase for 1 hour at condition specified in the table below, the swatches was removed from the beakers and transferred into the inactivation solution with 2 g/L of sodium carbonate and kept at 85° C. for 10 min. Then the swatches were rinsed in hot water for 2 times and in cold water for 2 times. And they were tumble-dried (AEG, LAVATHERM 37700, Germany) for 1 hour, conditioned for 24 hours at 65% relative humidity, 21° C. prior to evaluation in weight loss and pilling notes.

Biotouch XC300 is a neutral cellulase product in the market, which performs well under temperature 20-50° C. As summarized in table 1, *Neurospora tetrasperma* GH45 was much stronger than Biotouch XC300 on protein basis: at 35° C. and pH 6.5, 0.032 mg enzyme protein of Nt Cel45/g fabric delivered similar performance by both pilling note and weight loss as 0.096 mg enzyme protein of Biotouch XC300/g fabric did.

Similarly, it was found that *Neurospora crassa* GH45 endoglucanse was stronger than Biotouch XC300 endoglucanase on protein basis: at 35° C. and pH 6.5, 0.032 mg enzyme protein of Nc Cel45/g fabric delivered significant improvement in pilling note than 0.064 mg enzyme protein of Biotouch XC300/g fabric did. Nc Cel45 showed superiority over protein purified from Biotouch XC300 for its higher pilling notes at similar weight loss level: with 0.5% weight loss, Nc Cel45 delivered a pilling note 2.4, while on contrast, protein purified from Biotouch XC300 only resulted at 1.5 in pilling.

TABLE 1

LOM biopolishing with *Neurospora crassa* GH45, *Neurospora tetrasperma* GH45 and Biotouch XC 300 at 35° C., pH 6.5

| Enzyme | Dosage (mg/g) | Weight loss (%) | Pilling notes |
|---|---|---|---|
| Blank | 0.000 | 0.0 | 1.5 |
|  | 0.032 | 0.4 | 1.5 |
| Biotouch XC300 | 0.064 | 0.5 | 1.6 |
|  | 0.096 | 1.1 | 3.5 |
| *Neurospora tetrasperma* GH45 | 0.032 | 1.1 | 3.4 |
|  | 0.064 | 2.0 | 3.9 |
|  | 0.096 | 2.4 | 3.9 |
| *Neurospora crassa* GH45 | 0.016 | 0.5 | 2.4 |
|  | 0.032 | 0.9 | 2.6 |
|  | 0.064 | 1.5 | 3.3 |

Note:
the weight loss was normalized by subtracting the weight loss of blank samples, respectively.

Example 15: Biopolishing with *Neurospora crassa* GH45, *Neurospora tetrasperma* GH45 and Biotouch XC 300 at Different Temperatures in Launder-O-Meter The *Neurospora crassa* GH45 endoglucanase (Nc Cel45), *Neurospora tetrasperma* GH45 endoglucanase (Nt Cel45) and the protein from commercially available product Biotouch XC300 were extensively tested at different temperatures for biopolishing in the present example after purification as described in Example 5, 11 and 12 respectively.

The fabric preparation and trial operation was similar to Example 14 except that several independent trials with different temperatures/dosages were conducted in this example.

As summarized in Table 2, all the three purified enzyme samples were confirmed to show similar temperature feature: best at 35° C. and gradually dropped in performance with the temperature increased to 45 and 55° C. Again it was proven that *Neurospora tetrasperma* GH45 and *Neurospora crassa* GH45 were stronger than the protein purified from Biotouch XC300 in all conditions tested here. For example, at 35° C., 0.048 mg enzyme protein of Nt Cel45 per gram of fabric delivered higher pilling notes than 0.096 mg enzyme protein purified from Biotouch XC300; and 0.064 mg Nc Cel45 per gram of fabric also delivered similar or higher pilling notes than 0.096 mg cellulase protein purified from Biotouch XC300 at both 35 and 45° C. Nt Cel45 and Nc Cel45 were also superior over protein purified from Biotouch XC300 in achieving a similar pilling note but at lower weight loss, for example, Nt Cel45 delivered a pilling note 3.9 with 0.9% weight loss, Nc Cel45 delivered a pilling note 3.3 with 0.5% weight loss, while on contrast, Biotouch XC 300 caused 1.1% weight loss to get a pilling note 3.5.

TABLE 2

LOM biopolishing with *Neurospora tetrasperma* GH45, *Neurospora crassa* GH45 and Biotouch XC 300 at pH 6.5 and different temperatures

| Enzyme | Temperature (° C.) | Weight loss (%) | Pilling notes |
|---|---|---|---|
| 0.048 mg *Neurospora tetrasperma* GH45/gram fabric | 35 | 1.8 | 4.0 |
|  | 45 | 0.9 | 3.9 |
|  | 55 | 0.4 | 2.4 |
| 0.064 mg *Neurospora crassa* GH45/gram fabric | 35 | 1.5 | 3.3 |
|  | 45 | 0.5 | 3.3 |
|  | 55 | −0.3 | 1.8 |
| 0.096 mg Biotouch XC300/gram fabric | 35 | 1.1 | 3.5 |
|  | 45 | 0.4 | 1.9 |
|  | 55 | −0.3 | 1.8 |

Note:
the weight loss was normalized by subtracting the weight loss of blank samples in the same trial, respectively.

Example 16: Biopolishing with *Neurospora crassa* GH45, *Neurospora tetrasperma* GH45 and Biotouch XC 300 at Different pHs in Launder-O-Meter The *Neurospora crassa* GH45 (Nc Cel45), *Neurospora tetrasperma* GH45 endoglucanase (Nt cel45) were extensively tested at 45° C. and different pHs for biopolishing in the present example after purification as described in previous Examples.

The fabric preparation and trial operation was similar to Example 14 except that different pHs were used as specified in the table below in this example.

As shown in Table 3, both *Neurospora tetrasperma* GH45 and *Neurospora crassa* GH45 worked well in a broad pH range from 5 to 7.5. 0.032 mg *Neurospora tetrasperma* GH45 per gram of fabric delivered pilling notes of 3.4 to 4.0, while 0.064 mg *Neurospora crassa* GH45 per gram of fabric delivered pilling notes of 3.8 to 3.9. The broad pH range of application of these two enzymes will enable the customers to produce high quality fabrics with great flexibility.

TABLE 3

LOM biopolishing with Neurospora tetrasperma GH45, Neurospora crassa GH45 and 45° C. and different pHs

| Enzyme | pH | Weight loss (%) | Pilling notes |
|---|---|---|---|
| blank | 6.5 | 0 | 1.1 |
| 0.032 mg Neurosporate trasperma GH45/gram fabric | 5.0 | 0.4 | 3.4 |
|  | 6.5 | 0.9 | 3.9 |
|  | 7.5 | 0.6 | 4.0 |
| 0.064 mg Neurospora crassa GH45/gram fabric | 5.0 | 1.6 | 3.9 |
|  | 7.5 | 1.4 | 3.8 |

Example 17: Denim Abrasion with Neurospora crassa GH45, Neurospora tetrasperma GH45 and Biotouch XC 300 at Different Temperatures in Launder-O-Meter The *Neurospora crassa* GH45 (Nc cel45), *Neurospora tetrasperma* GH45 (Nt cel 45) purified from previous Examples were evaluated for denim abrasion in the present example. The cellulase protein purified from the commercially available product Biotouch XC300 was also tested as the benchmark.

Raw denim was desized and cut into 16 cm tall and 24 cm long. The denim was cut and sewn, forming a tube with height of 12.5 cm and weight of about 18 g. The tubes were placed in a conditioned room (65% relative humidity, 21° C.) for 24 hours before they were numbered, weighed by the analytical balance and recorded. One conditioned tube was placed in each beaker, with the blue side facing inward. For each beaker, 30 big nuts (M6M-SR-A4-80, acid proof, M10 DIN 934), 10 small nuts (M6M-SR-A4-80, acid proof, M6 DIN 934), 7 big star magnets (diameter of 17 mm, item no. 3-CO-411117, Cowie, Schweiz via Bie & Berntsen), and 3 small star magnets (diameter of 14 mm, item no. 3-CO-11117, Cowie, Schweiz via Bie & Berntsen) were used to supply the mechanical aids. Then the buffers prepared as described in the media part and the enzyme solutions were added according to Table 4, based on the calculation of actual fabric weights, to make a total volume around 80 ml, which would create a liquid to fabric ratio of 3.8:1 (v/w).

The Launder-O-Meter (LOM) machine was started after the required program as below was chosen, and it would hold when the temperature reached the pre-set temperature, e.g. 35° C., 45° C. or 55° C. Each beaker was fitted with a lid lined with 2 neoprin gaskets and close tightly with the metal clamping device. The beakers were loaded into the preheated LOM. Metal racks were used to accommodate and secure 6 beakers, in the horizontal position, in each of the 4 drum positions. The LOM lid was closed and the washing program was continued and the timing was initiated. 2 hours later, all beakers were removed from LOM and the denim samples were transferred to the inactivation solution (2 g/L sodium carbonate) at 85° C. for 10 minutes. Then the swatches were rinsed in hot water for 2 times and in cold water for 2 times. The denim samples were tumble-dried (AEG, LAVATHERM 37700, Germany) for 1 hour, and then conditioned at 65% relative humidity, 21° C. for 24 hours prior to evaluation.

The abrasion and backstaining level of the denim samples were determined by measuring the reflectance before and after the endoglucanse treatment with pre-calibrated Data-Color SF450X. For both L* and b*, four readings were taken for each fabric and the average of the four readings was used. The abrasion level was evaluated with the index CIE L* of the blue side of the sample, and the backstaining level was evaluated with the index CIE b* of the back of the sample. As summarized in Table 4, it was proven that in denim abrasion, Nt Cel45 was stronger than cellulase purified from Biotouch XC 300, i.e, 0.032 mg Nt Cel45 per gram of fabric delivered 4.9 and 5.0 in L* value increase on denim face at 35 and 55° C. respectively, while on contrast, 0.064 mg cellulase purified from Biotouch XC 300 per gram of fabric can only delivered 4.7 and 3.1 in L* value increase respectively.

Nt Cel45 was also superior over cellulase in Biotouch XC300 for its consistent denim abrasion performance over a broad range of temperature. In actual industry application, this feature will give the users more flexibility in operation and better quality in textile products. Nc Cel45 was also better than cellulase purified from Biotouch XC300 since half dosage of *Neurospora crassa* Cel45a delivered just slightly lower denim abrasion performance than the cellulase from Biotouch XC300.

TABLE 4

Denim abrasion by Neurospora tetrasperma GH45, Neurospora crassa GH45 and Biotouch XC 300 in LOM at pH 6.5, 35 or 55° C., 2 hours

| Temperature (° C.) | Enzyme | Dosage (mg enzyme/ g fabric) | delta L* | delta b* |
|---|---|---|---|---|
| 35 | Blank | 0 | 1.3 | −1.4 |
|  | Neurospora tetrasperma GH45 | 0.032 | 4.9 | −3.5 |
|  | Neurospora crassa GH45 | 0.032 | 3.8 | −3.5 |
|  | Biotouch XC300 | 0.064 | 4.7 | −3.3 |
| 55 | Blank | 0 | 2.3 | −1.8 |
|  | Neurospora tetrasperma GH45 | 0.032 | 5.0 | −2.8 |
|  | Neurospora crassa GH45 | 0.032 | 2.3 | −1.7 |
|  | Biotouch XC300 | 0.064 | 3.1 | −2.3 |

Note:
average of triple samples for each condition.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for processing a textile, comprising treating the textile with a polypeptide having endoglucanase activity,
wherein the polypeptide comprises a sequence having at least 95% sequence identity to amino acids 22 to 293 of SEQ ID NO: 2,
and wherein the method is conducted at a temperature in the range of 25-55° C. and at a pH in the range of 5 to 7.5.

2. The method of claim 1, wherein the polypeptide having endoglucanase activity comprises a sequence having a substitution, deletion, and/or insertion of 1 to 10 amino acids of amino acids 22 to 293 SEQ ID NO: 2.

3. The method of claim 1, wherein the polypeptide having endoglucanase activity is obtained from a species of the genus *Neurospora*.

4. The method of claim 3, wherein the polypeptide having endoglucanase activity is obtained from *Neurospora tetrasperma* or *Neurospora crassa*.

5. The method of claim 1, wherein the polypeptide having endoglucanase activity comprises or consists of SEQ ID NO: 2 or SEQ ID NO: 4.

6. The method of claim 1, wherein the polypeptide having endoglucanase activity comprises or consists of amino acids 22 to 293 of SEQ ID NO: 2 or amino acids 22 to 293 of SEQ ID NO: 4.

7. The method of claim 1, wherein the textile is cellulose-containing textile.

8. The method of claim 1, wherein the textile comprises cotton, viscose, rayon, ramie, linen, or lyocell.

9. The method of claim 1, wherein the textile comprises synthetic fibers.

10. The method of claim 1, wherein the method is conducted at a temperature in the range of 30-45° C.

11. The method of claim 1, wherein the method is conducted at a pH in the range of 6 to 7.

12. The method of claim 1, wherein the method is conducted at a temperature in the range of 30-45° C. and at a pH in the range of 6 to 7.

13. The method of claim 1, wherein the polypeptide comprises a sequence having at least 97% sequence identity to amino acids 22 to 293 of SEQ ID NO: 2.

14. The method of claim 1, wherein the polypeptide comprises a sequence having at least 98% sequence identity to amino acids 22 to 293 of SEQ ID NO: 2.

15. The method of claim 1, wherein the polypeptide comprises a sequence having at least 99% sequence identity to amino acids 22 to 293 of SEQ ID NO: 2.

16. The method of claim 1, wherein the polypeptide having endoglucanase activity comprises a sequence having a substitution, deletion, and/or insertion of 1 or 2 amino acids of amino acids 22 to 293 SEQ ID NO: 2.

17. The method of claim 1, wherein the method is applied in a biopolishing process.

18. The method of claim 1, wherein the method is applied in a biostoning process.

* * * * *

SEQUENCE LISTING

<160> NUMBER OF SEQ ID NOS: 10

<210> SEQ ID NO 1
<211> LENGTH: 935

```
<212> TYPE: DNA
<213> ORGANISM: Neurospora tetrasperma

<400> SEQUENCE: 1
atgcgctcct ccactgttct gcaaaccggg ctagtggccg ctcttccctt cgccgttcag      60
gccgcgtccg gatccggcca gtccaccaga tattgggact gctgcaaacc atcttgctcc     120
tggtccggca aggcttctgt caaccgaccc gtcctcgctt gcgatgcaaa caacaacccc     180
ctgagcgacg ccagtgtcaa gtctggatgt gacggcggtt ctgcatacac ctgtgccaac     240
aactcaccat gggcggtgaa cgaccagctc tcctacggct tgctgccac gaaactcagt      300
ggtggaaccg agtcgtcttg gtgctgtgcc tgttatgcgt gagtttcgcg tcaacagctg     360
ggtatcactt gatggctaat ttatactgca gccttacctt cacttcgggt cctgttgctg     420
gcaagaccat ggtcgttcag tctaccagta ccggcggtga tctcggctcc aaccacttcg     480
atatcaacat gcccggcggc ggcgtcggcc tgtttgatgg ctgtacacga cagtttggcg     540
gtctccccgg cgctcaatat ggcggcatca gctcccgcag ccagtgcgat tcattccctg     600
ccgcgctcaa gcccggttgc cagtggcgct tcgactggtt ccagaacgcc gacaacccca     660
acttcacctt caagcaggtc caatgcccat ccgagctcac ctcccgcacc ggctgcaagc     720
gaaacgacga ctctcaattc cctgtcttca ctccgccctc tggtggaggc accaaccccc     780
tactccgac aacccctccc tcttcaggcg gcggttccgg atgtacgcg gataaatacg       840
ctcagtgtgg cggctcgggg tggtctggct gcaccaactg cccgtctgga tcgacctgca     900
agactatcaa cgattattac caccagtgtg cctaa                                935

<210> SEQ ID NO 2
<211> LENGTH: 293
<212> TYPE: PRT
<213> ORGANISM: Neurospora tetrasperma

<400> SEQUENCE: 2

Met Arg Ser Ser Thr Val Leu Gln Thr Gly Leu Val Ala Ala Leu Pro
1               5                  10                  15

Phe Ala Val Gln Ala Ala Ser Gly Ser Gly Gln Ser Thr Arg Tyr Trp
            20                  25                  30

Asp Cys Cys Lys Pro Ser Cys Ser Trp Ser Gly Lys Ala Ser Val Asn
        35                  40                  45

Arg Pro Val Leu Ala Cys Asp Ala Asn Asn Asn Pro Leu Ser Asp Ala
    50                  55                  60

Ser Val Lys Ser Gly Cys Asp Gly Gly Ser Ala Tyr Thr Cys Ala Asn
65                  70                  75                  80

Asn Ser Pro Trp Ala Val Asn Asp Gln Leu Ser Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn His Phe Asp Ile
    130                 135                 140

Asn Met Pro Gly Gly Gly Val Gly Leu Phe Asp Gly Cys Thr Arg Gln
145                 150                 155                 160

Phe Gly Gly Leu Pro Gly Ala Gln Tyr Gly Gly Ile Ser Ser Arg Ser
                165                 170                 175

Gln Cys Asp Ser Phe Pro Ala Ala Leu Lys Pro Gly Cys Gln Trp Arg
```

```
                180                 185                 190

Phe Asp Trp Phe Gln Asn Ala Asp Asn Pro Asn Phe Thr Phe Lys Gln
            195                 200                 205

Val Gln Cys Pro Ser Glu Leu Thr Ser Arg Thr Gly Cys Lys Arg Asn
        210                 215                 220

Asp Asp Ser Gln Phe Pro Val Phe Thr Pro Ser Gly Gly Gly Thr
225                 230                 235                 240

Asn Pro Ser Thr Pro Thr Thr Pro Pro Ser Gly Gly Gly Ser Gly
                245                 250                 255

Cys Thr Ala Asp Lys Tyr Ala Gln Cys Gly Gly Ser Gly Trp Ser Gly
            260                 265                 270

Cys Thr Asn Cys Pro Ser Gly Ser Thr Cys Lys Thr Ile Asn Asp Tyr
        275                 280                 285

Tyr His Gln Cys Ala
        290

<210> SEQ ID NO 3
<211> LENGTH: 935
<212> TYPE: DNA
<213> ORGANISM: Neurospora crassa

<400> SEQUENCE: 3
atgcgctcct ccactattct gcaaaccggg ctagtggccg ctcttccttt cgccgtccag      60
gctgcttccg gatccggcca gtccaccaga tattgggact gctgcaaacc atcttgctcc    120
tggtccggca aggctcctgt caaccgaccc gtcctcgctt cgacgcaaa caacaacccc     180 ctgagcgacg ccagtgtcaa gtctggatgt gatggcggtt ctgcatacac ctgtgccaac    240
aactcaccat gggcggtgaa cgaccagctc tcctacggct tgccgccac gaaactcagt    300 ggtggaaccg agtcatcttg gtgctgtgcc tgttatgcgt gagtttctct tcaactcttg    360
ggtatcactc gatggctaac ttttactgca gccttacctt cacttcgggc cctgttgctg    420
gcaagacctt ggtcgttcag tctaccagta ccggcggtga tctcggctcc aaccacttcg    480
atatcaacat gcccggcggc ggcgtcggcc tgtttgatgg atgtaaacga cagttcggcg    540
gtctccccgg cgctcaatat ggcggcatca gctcccgcag ccagtgcgac tcgttccctg    600
ccgctctcaa gcccggttgc cagtggcgct cgactggtt ccagaacgcc gataacccga    660
acttcacctt caagcaggtc caatgcccat ccgagctcac atcccgcacc ggctgcaagc    720
gaaacgacga ctcccaattc cctgtcttca ctccgcgcctc tggtggaggc agtaaccccct  780 ctactccgac aaccctcccc tcttcaggcg gcggttccgg atgtacagcg ataaatacg    840 ctcaatgtgg tggctcgggg tggtctggct gcaccaactg cccgtctgga tcgacctgca   900
agactatcaa cgattattac catcagtgtg cctga                                935

<210> SEQ ID NO 4
<211> LENGTH: 293
<212> TYPE: PRT
<213> ORGANISM: Neurospora crassa

<400> SEQUENCE: 4

Met Arg Ser Ser Thr Ile Leu Gln Thr Gly Leu Val Ala Ala Leu Pro
1               5                   10                  15

Phe Ala Val Gln Ala Ala Ser Gly Ser Gly Gln Ser Thr Arg Tyr Trp
            20                  25                  30

Asp Cys Cys Lys Pro Ser Cys Ser Trp Ser Gly Lys Ala Pro Val Asn
        35                  40                  45
```

```
Arg Pro Val Leu Ala Cys Asp Ala Asn Asn Pro Leu Ser Asp Ala
    50                  55                  60

Ser Val Lys Ser Gly Cys Asp Gly Gly Ser Ala Tyr Thr Cys Ala Asn
65                  70                  75                  80

Asn Ser Pro Trp Ala Val Asn Asp Gln Leu Ser Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ala Gly Lys Thr Leu Val Val
        115                 120                 125

Gln Ser Thr Ser Thr Gly Gly Asp Leu Gly Ser Asn His Phe Asp Ile
    130                 135                 140

Asn Met Pro Gly Gly Gly Val Gly Leu Phe Asp Gly Cys Lys Arg Gln
145                 150                 155                 160

Phe Gly Gly Leu Pro Gly Ala Gln Tyr Gly Gly Ile Ser Ser Arg Ser
                165                 170                 175

Gln Cys Asp Ser Phe Pro Ala Ala Leu Lys Pro Gly Cys Gln Trp Arg
            180                 185                 190

Phe Asp Trp Phe Gln Asn Ala Asp Asn Pro Asn Phe Thr Phe Lys Gln
        195                 200                 205

Val Gln Cys Pro Ser Glu Leu Thr Ser Arg Thr Gly Cys Lys Arg Asn
    210                 215                 220

Asp Asp Ser Gln Phe Pro Val Phe Thr Pro Pro Ser Gly Gly Gly Ser
225                 230                 235                 240

Asn Pro Ser Thr Pro Thr Thr Pro Ser Ser Gly Gly Ser Gly
                245                 250                 255

Cys Thr Ala Asp Lys Tyr Ala Gln Cys Gly Gly Ser Gly Trp Ser Gly
            260                 265                 270

Cys Thr Asn Cys Pro Ser Gly Ser Thr Cys Lys Thr Ile Asn Asp Tyr
        275                 280                 285

Tyr His Gln Cys Ala
    290

<210> SEQ ID NO 5
<211> LENGTH: 41
<212> TYPE: DNA
<213> ORGANISM: Artificial Sequence
<220> FEATURE:
<223> OTHER INFORMATION: synthetic construct

<400> SEQUENCE: 5
acacaactgg ggatccacca tgcgctcctc cactgttctg c                           41

<210> SEQ ID NO 6
<211> LENGTH: 43
<212> TYPE: DNA
<213> ORGANISM: Artificial Sequence
<220> FEATURE:
<223> OTHER INFORMATION: synthetic construct

<400> SEQUENCE: 6
agatctcgag aagcttaggc acactggtgg taataatcgt tga                         43

<210> SEQ ID NO 7
<211> LENGTH: 37
<212> TYPE: DNA
<213> ORGANISM: Artificial Sequence
<220> FEATURE:
```

```
<223> OTHER INFORMATION: synthetic construct

<400> SEQUENCE: 7
actggattta ccatgcgctc ctccactatt ctgcaaa                          37

<210> SEQ ID NO 8
<211> LENGTH: 34
<212> TYPE: DNA
<213> ORGANISM: Artificial Sequence
<220> FEATURE:
<223> OTHER INFORMATION: synthetic construct

<400> SEQUENCE: 8
tcacctctag ttaatcaggc acactgatgg taat                             34

<210> SEQ ID NO 9
<211> LENGTH: 17
<212> TYPE: DNA
<213> ORGANISM: Artificial Sequence
<220> FEATURE:
<223> OTHER INFORMATION: synthetic construct

<400> SEQUENCE: 9
tgtcccttgt cgatgcg                                                17

<210> SEQ ID NO 10
<211> LENGTH: 17
<212> TYPE: DNA
<213> ORGANISM: Artificial Sequence
<220> FEATURE:
<223> OTHER INFORMATION: synthetic construct

<400> SEQUENCE: 10
cacatgactt ggcttcc                                                17
```